(12) United States Patent
Li et al.

(10) Patent No.: US 10,134,123 B2
(45) Date of Patent: Nov. 20, 2018

(54) METHODS, SYSTEMS, AND APPARATUSES FOR INSPECTING GOODS (71) Applicants: Tsinghua University, Beijing (CN); NUCTECH COMPANY LIMITED, Beijing (CN)

(72) Inventors: Yuanjing Li, Beijing (CN); Ziran Zhao, Beijing (CN); Yaohong Liu, Beijing (CN); Qili Wang, Beijing (CN); Qiang Li, Beijing (CN); Jianping Gu, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 90 days.

(21) Appl. No.: 15/278,101

(22) Filed: Sep. 28, 2016

(65) Prior Publication Data
US 2017/0178312 A1    Jun. 22, 2017

(30) Foreign Application Priority Data

Dec. 16, 2015   (CN) .......................... 2015 1 0941150

(51) Int. Cl.
*G06K 9/00* (2006.01)
*G06T 7/00* (2017.01)
(Continued)

(52) U.S. Cl.
CPC ........... *G06T 7/0004* (2013.01); *G01N 23/04* (2013.01); *G06K 9/48* (2013.01); *G06T 7/0085* (2013.01);
(Continued)

(58) Field of Classification Search
USPC ....................................................... 382/141
See application file for complete search history.

(56) References Cited

U.S. PATENT DOCUMENTS

2006/0243071 A1   11/2006  Sagi-Dolev
2010/0046704 A1    2/2010  Song et al.
(Continued)

FOREIGN PATENT DOCUMENTS

WO    2015/144706 A1   10/2015

OTHER PUBLICATIONS

Al-Najdawi, "A Concealed Ammo Detection System for Passengers Luggage Screening", 2014 International Conference on Multimedia Computing and Systems (ICMCS), IEEE, Apr. 14, 2014, pp. 159-164, XP032651785.
(Continued)

*Primary Examiner* — Jerome Grant, II
(74) *Attorney, Agent, or Firm* — Morgan, Lewis & Bockius LLP (57) ABSTRACT

The present disclosure provides a method and a system for inspecting goods. The method comprises steps of: obtaining a transmission image of inspected goods; processing the transmission image to obtain a suspicious region; extracting local texture features of the suspicious region and classifying the local texture features of the suspicious region based on a pre-created model to obtain a classification result; extracting a contour line shape feature of the suspicious region and comparing the contour line shape feature with a pre-created standard template to obtain a comparison result; and determining that the suspicious region contains a high atomic number matter based on the classification result and the comparison result.

7 Claims, 9 Drawing Sheets

(51) Int. Cl.
*G06T 7/40* (2017.01)
*G06K 9/48* (2006.01)
*G01N 23/04* (2018.01)

(52) U.S. Cl.
CPC .......... *G06T 7/40* (2013.01); *G01N 2223/401* (2013.01); *G01N 2223/626* (2013.01); *G06T 2207/10116* (2013.01)

(56) References Cited

U.S. PATENT DOCUMENTS

| | | | |
|---|---|---|---|
| 2010/0295689 | A1 | 11/2010 | Armistead, Jr. et al. |
| 2012/0059517 | A1* | 3/2012 | Nomura ................. B25J 9/1612 700/259 |
| 2013/0286219 | A1* | 10/2013 | Yeh ........................... G06T 7/80 348/187 |
| 2015/0286883 | A1* | 10/2015 | Xu ..................... G06K 9/00228 382/103 |
| 2016/0232678 | A1* | 8/2016 | Kurz ................. G06F 17/30247 |
| 2017/0061686 | A1* | 3/2017 | Yu ......................... G06T 19/003 |
| 2017/0076438 | A1* | 3/2017 | Kottenstette ....... G06K 9/00637 |
| 2017/0103513 | A1 | 4/2017 | Heilmann |
| 2017/0116734 | A1* | 4/2017 | Van Leeuwen ....... G06T 7/0014 |
| 2017/0189797 | A1* | 7/2017 | Muthyala ............... A63F 13/655 |
| 2017/0358078 | A1* | 12/2017 | Hoff ...................... G06T 7/0012 |
| 2018/0005035 | A1* | 1/2018 | Bogolea ............. G06K 9/00671 |

OTHER PUBLICATIONS

Extended European Search Report (EESR) dated Jun. 21, 2017, issued in corresponding European Patent Application No. 16191264.7.

Written Opinion in corresponding Singapore Patent Application No. 11201709757V dated Mar. 20, 2018.

* cited by examiner

METHODS, SYSTEMS, AND APPARATUSES FOR INSPECTING GOODS

TECHNICAL FIELD

The present disclosure relates to automatic detection of a suspicious object in a radiation image, and more particularly, to methods and systems for inspecting high atomic number matters in a large container scanning system.

BACKGROUND

It is of great significance to crack down on carriage and transportation of high atomic number matters, such as nuclear materials, nuclear weapons and radioactive dispersal devices. Since the 911 incident in the U.S., prevention and handling of nuclear and radioactive terrorist attacks have become a significant social security issue the countries all over the world have to face. Compared with other terrorist attacks, while terrorist attacks with crudely made nuclear devices happen at a relatively low probability, their consequences will be very severe, including not only massive casualties, but also damages to economic development and even panics and instabilities of the society. Hence, the surveillance on nuclear materials for producing nuclear devices has become a nuclear security issue the global society has paid great attention to.

Since the beginning of the $21^{st}$ century, there have been hundreds of millions of containers transferred all over the world every year. Recently, the terrorism has become increasingly rampant and there are increasingly higher risks of nuclear and radioactive terrorist attacks. Terrorists may hide weapons of mass destruction or radioactive dispersal devices in containers carrying commercial goods for transportation to the destination of the attack. Hence, there is a need for inspecting whether there are any hidden nuclear materials, nuclear weapons or radioactive dispersal devices, so as to reduce security risks while ensuring fast and stable commercial transportations.

SUMMARY

In view of the one or more problems in the prior art, the present disclosure provides a method and a system for goods inspection.

According to an aspect of the present disclosure, a method for goods inspection is provided. The method includes the steps of: obtaining a transmission image of inspected goods; processing the transmission image to obtain a suspicious region; extracting local texture features of the suspicious region and classifying the local texture features of the suspicious region based on a pre-created model to obtain a classification result; extracting a contour line shape feature of the suspicious region and comparing the contour line shape feature with a pre-created standard template to obtain a comparison result; and determining that the suspicious region contains a high atomic number matter based on the classification result and the comparison result.

In some embodiments, the method further includes: obtaining equivalent atomic number information of the suspicious region. The step of determining includes determining that the suspicious region contains a high atomic number matter based on the classification result, the comparison result and the equivalent atomic number information.

In some embodiments, the step of processing the transmission image to obtain the suspicious region includes: enhancing a contrast of the transmission image; performing a plurality of binarization operations on the contrast-enhanced transmission image; and deriving a connected region of the binarized transmission image and determining a border of the connected region.

In some embodiments, the step of extracting the contour line shape feature of the suspicious region includes: deriving a contour line of the suspicious region using an edge extraction algorithm and deriving a $(\theta,\rho)$ feature curve of the contour line.

In some embodiments, the step of comparing the contour line shape feature with the pre-created standard template includes: calculating a distance and an amplitude consistency between the $(\theta,\rho)$ feature curve of the contour line and the standard template and a $\theta$ jump value of the $(\theta,\rho)$ feature curve of the contour line; and comparing the distance, the amplitude consistency and the $\theta$ jump value with respective thresholds.

In some embodiments, a contour line of a suspicious object in the suspicious region is obtained using an edge feature extraction algorithm, a centroid of a region enclosed by the contour line is calculated, and then a $(\theta,\rho)$ feature curve of the contour line with respect to the calculated centroid as a coordinate origin is derived.

In some embodiments, the method further includes: highlighting a region considered to be the high atomic number matter in the transmission image.

In another aspect of the present disclosure, a system for inspecting goods is provided. The system includes: an X-ray scanning device configured to obtain a transmission image of inspected goods; and a data processing device configured to: process the transmission image to obtain a suspicious region; extract local texture features of the suspicious region and classify the local texture features of the suspicious region based on a pre-created model to obtain a classification result; extract a contour line shape feature of the suspicious region and compare the contour line shape feature with a pre-created standard template to obtain a comparison result; and determine that the suspicious region contains a high atomic number matter based on the classification result and the comparison result.

In yet another embodiment of the present disclosure, an apparatus for inspecting goods is provided. The apparatus includes: means for processing a transmission image of inspected goods to obtain a suspicious region; means for extracting local texture features of the suspicious region and classifying the local texture features of the suspicious region based on a pre-created model to obtain a classification result; means for extracting a contour line shape feature of the suspicious region and comparing the contour line shape feature with a pre-created standard template to obtain a comparison result; and means for determining that the suspicious region contains a high atomic number matter based on the classification result and the comparison result.

With the above solutions, it is possible to automatically inspect a high atomic number matter in the goods. For example, it is possible to determine whether there is any high atomic number matter hidden in a container, such as nuclear materials, nuclear weapons or radioactive dispersal devices. In this way, the work load for manual image detection can be reduced, such that the operation efficiency can be improved and missing or false detections of suspicious object regions can be reduced.

BRIEF DESCRIPTION OF THE DRAWINGS

To understand the present disclosure in a better way, a detailed description of the present disclosure will be given with reference to the following drawings, in which.

Not all of the circuits or structures in the embodiments are shown in the figures. Throughout all the figures, the same reference signs are used to represent the same or similar components or features.

DETAILED DESCRIPTION

Specific embodiments of the present disclosure will be described in detail below. It should be noted that the embodiments herein are used for illustration only, without limiting the present disclosure. Hereinafter, to provide a thorough understanding of the present disclosure, numerous specific details are set forth. However, it would be obvious for one ordinarily skilled in the art that the present disclosure can be practiced without these specific details. In other examples, known structures, materials, or methods are not described in detail to avoid any possible obfuscation of the present disclosure.

Throughout the specification, the reference to "one embodiment," "an embodiment," "one example" or "an example" means that the specific features, structures or properties described in conjunction with the embodiment or example are included in at least one embodiment of the present disclosure. Therefore, the phrases "in one embodiment," "in an embodiment," "in one example" or "in an example" presented in various positions throughout the specification may not necessarily refer to the same embodiment or example. Furthermore, specific features, structures or properties may be combined into one or more embodiments or examples in any appropriate combination and/or sub-combination. Moreover, it should be understood for those skilled in the art that the term "and/or" used herein means any and all combinations of one or more listed items.

In order to solve the problem associated with fast and accurate detection of a high atomic number matter in goods, the present disclosure proposes to determine whether a suspicious region of inspected goods contains a high atomic number matter based on a local texture feature and/or contour line shape feature of the suspicious region. For example, a ($\theta$,$\rho$) feature is used to describe a shape feature of the suspicious object and a Local Binary Pattern (LBP) feature is used to describe a texture feature of the suspicious object. In another embodiment, e.g., in a dual energy system, effective atomic number information can be used for further determination. In this way, by using the texture feature of the image, the edge information and/or material information of the suspicious object, the detection of the high atomic number matter can be simplified, such that the calculation time can be shortened and false detections can be reduced.

Figure 1A:
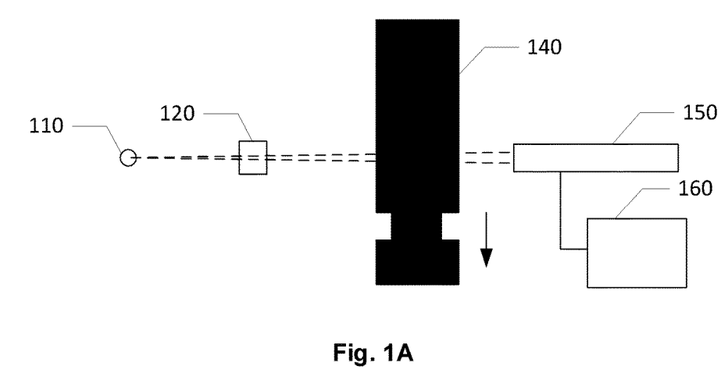
FIG. 1A and FIG. 1B are schematic diagrams each showing a system for inspecting goods according to an embodiment of the present disclosure.
Figure 1B:
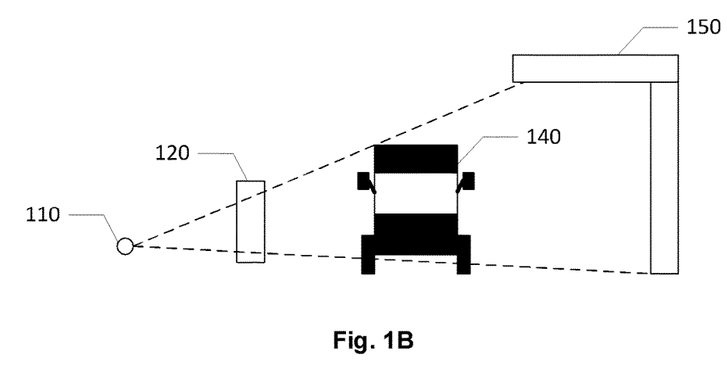

FIG. 1A and FIG. 1B are schematic diagrams each showing an inspection system according to an embodiment of the present disclosure. FIG. 1A shows a top view of the inspection system and FIG. 1B shows a front view of the inspection system. As shown in FIG. 1A and FIG. 1B, a radiation source 110 generates an X-ray, which is subjected to calibration by a calibrator 120 and then used for security inspection of a moving container truck 140. The ray penetrates the truck and is received by a detector 150. A transmission image is obtained at a data processing device 160, such as a computer, and the transmission image is processed to obtain a determination result.

Figure 2:
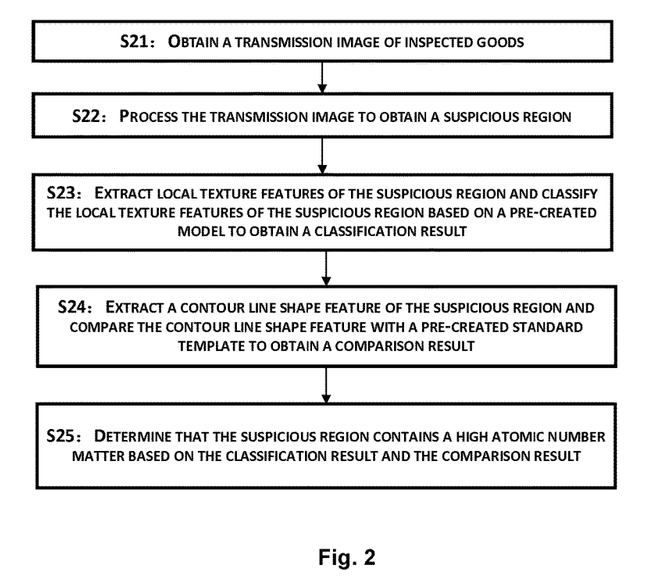
FIG. 2 is a flowchart illustrating a method for inspecting goods according to an embodiment of the present disclosure.

FIG. 2 is a flowchart illustrating a method for inspecting goods according to an embodiment of the present disclosure. As shown in FIG. 2, according to an embodiment of the present disclosure, at step S21, a transmission image of a container truck 140 is obtained by means of scanning. Then, at step S22, the transmission image is processed by a data processing device 160 to obtain a suspicious region.

At step S23, local texture features of the suspicious region are extracted and classified based on a pre-created model to obtain a classification result. Then, at step S24, the data processing device 160 extracts a contour line shape feature of the suspicious region and compares the contour line shape feature with a pre-created standard template to obtain a comparison result. Finally at step S25, it is determined that the suspicious region contains a high atomic number matter based on the classification result and the comparison result.

Figure 3:
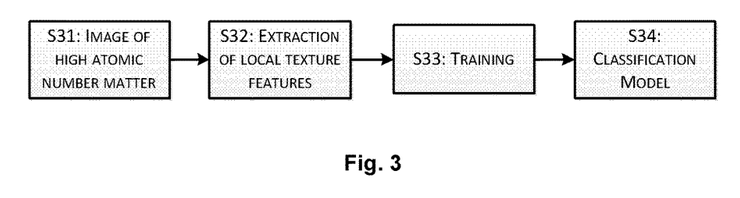
FIG. 3 is a flowchart illustrating a process for creating a classification model in the solution according to an embodiment of the present disclosure.
Figure 6:
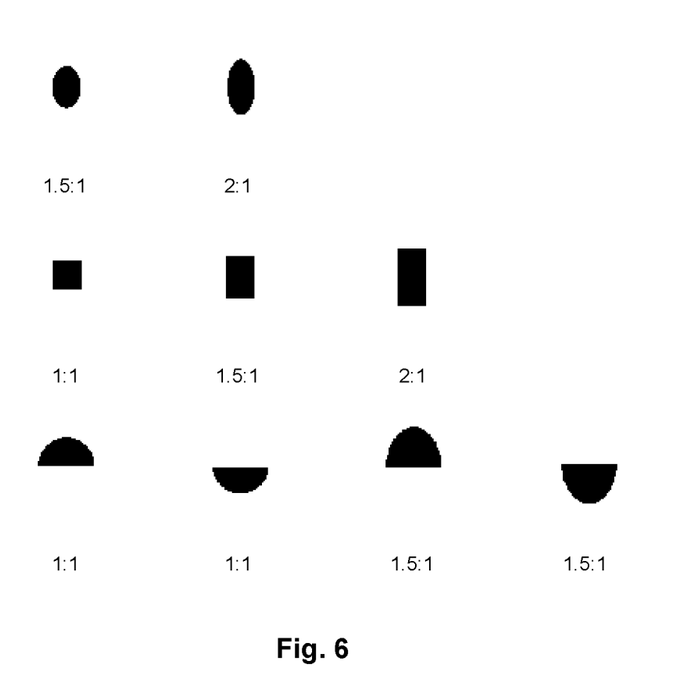
FIG. 6 is a schematic diagram showing a model of a high atomic number matter as used in the solution according to an embodiment of the present disclosure.
Figure 7A:
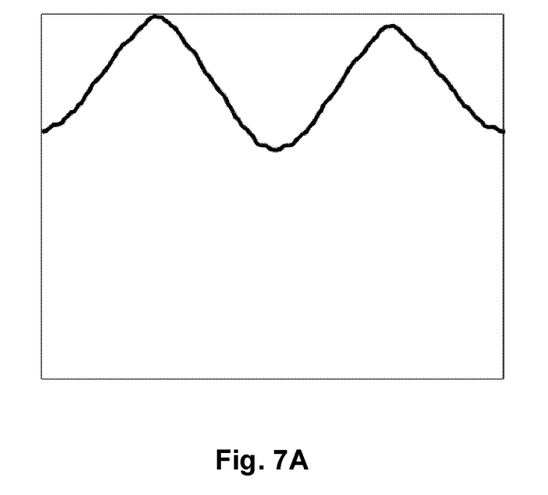
FIGS. 7A, 7B, 7C, 7D, 7E, 7F, 7G, 7H, and 7I are schematic diagrams each showing a ($\theta$,$\rho$) feature curve of a model of a high atomic number matter as used in the solution according to an embodiment of the present disclosure.
Figure 7B:
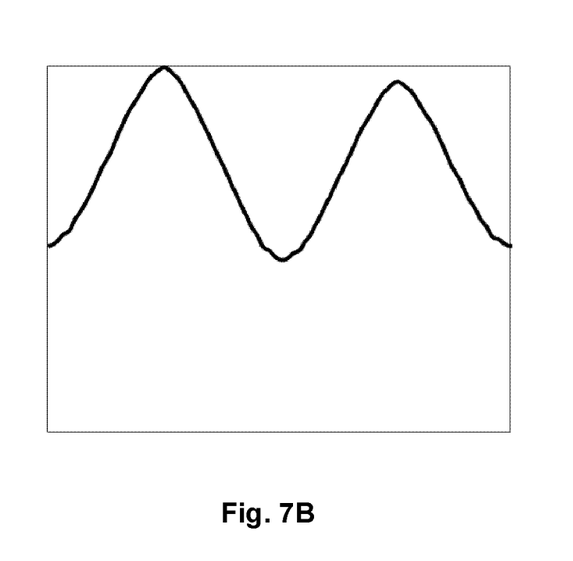
Figure 7C:
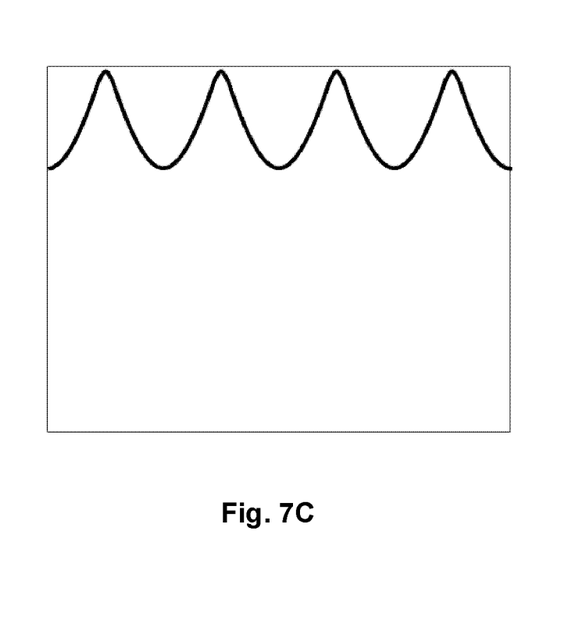
Figure 7D:
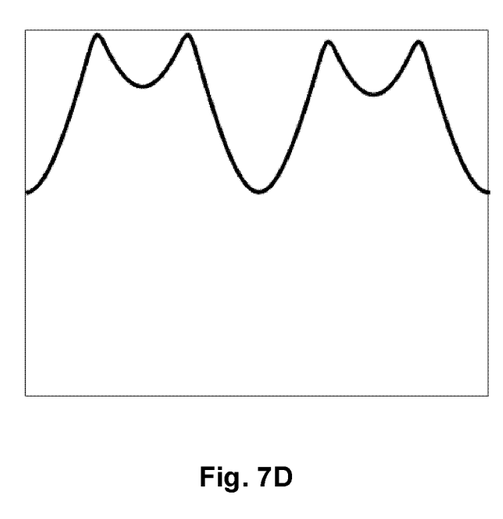
Figure 7E:
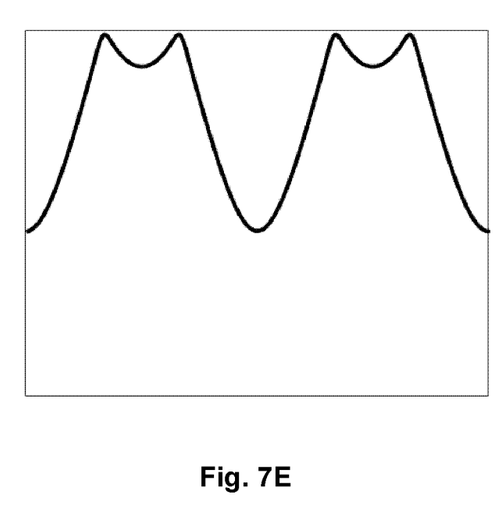
Figure 7F:
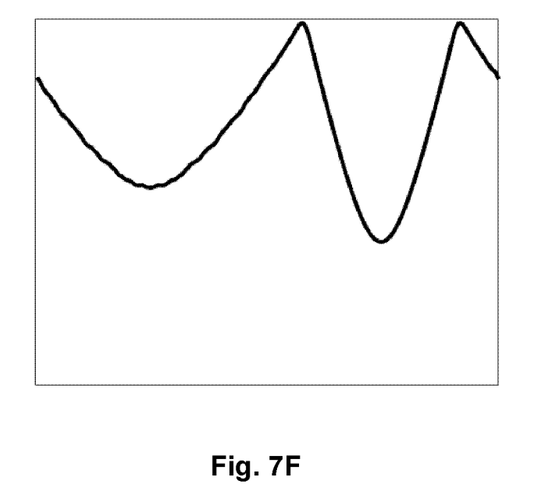
Figure 7G:
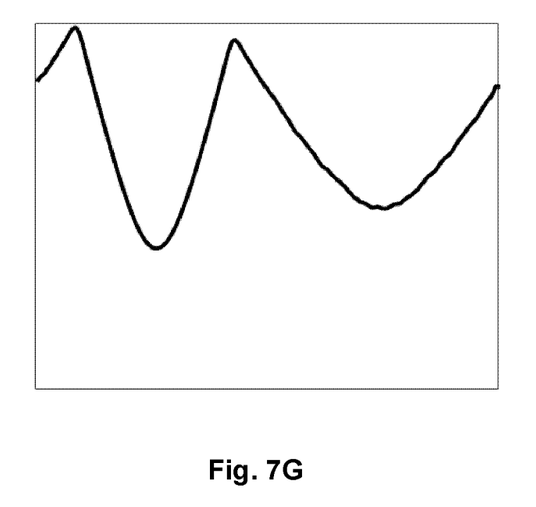
Figure 7H:
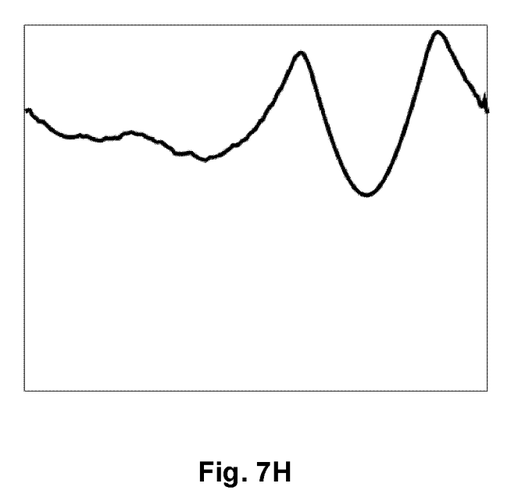
Figure 7I:
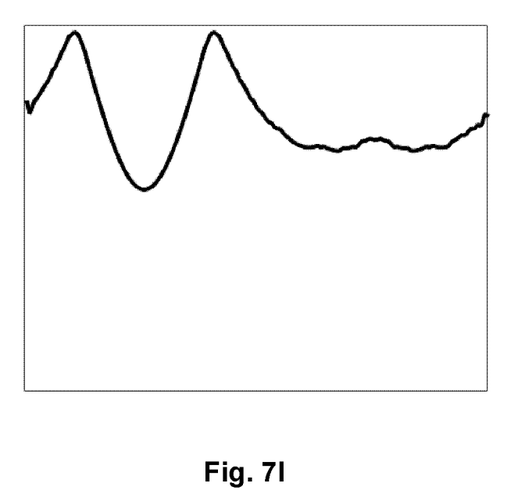

FIG. 3 is a flowchart illustrating a process for creating a classification model in the solution according to an embodiment of the present disclosure. At step S31, an image of a high atomic number matter is inputted. At step S32, local texture features, e.g., LBP features, of the image are extracted. A LBP feature is an operator for describing a local texture of an image and has advantages such as rotation invariance and gray scale invariance. Since nuclear materials, nuclear weapons or radioactive dispersal devices and their masking devices have regular shapes, such as cube, sphere or cylinder, a large number of suspicious regions can be obtained in the process of image binarization for deriving a connected region. Substantially all the high atomic number analog matters are included in a small fraction of these regions. FIG. 6 shows image regions containing high atomic number matters. These regions are stored, marked and classified. Those regions containing no high atomic number matters are classified as one class, and those containing high atomic number matters are classified, in a finer way, based on types of object contour lines into circle class, ellipse class, rectangle class, parallelogram class, horizontal half-circle class and vertical half-circle glass. That is, there are seven classes in total. Then, the LBP features are extracted. At step S33, the LBP features are used for training. Next, at step S34, a classification model is obtained. While in the above embodiment the high atomic number matters are classified into seven classes, it can be appreciated by those skilled in the art that the shapes of the high atomic number matters can be classified into different numbers of classes.

Figure 4:
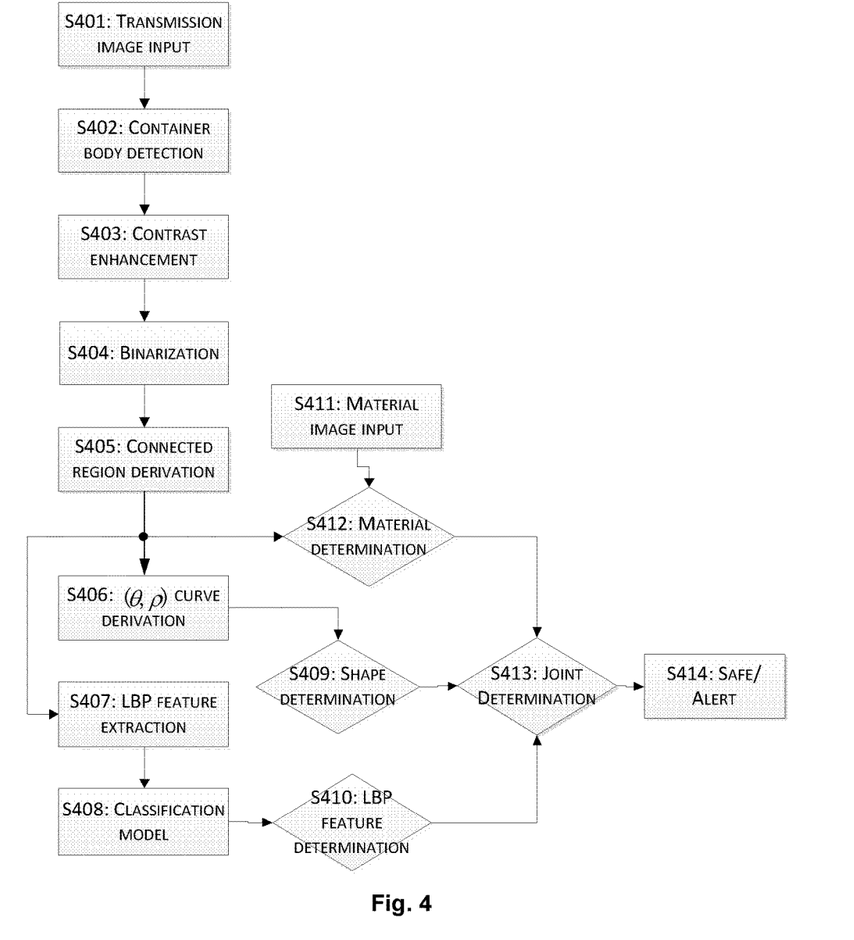
FIG. 4 is a flowchart illustrating a method for inspection using a created model in a dual energy mode according to an embodiment of the present disclosure.
Figure 5:
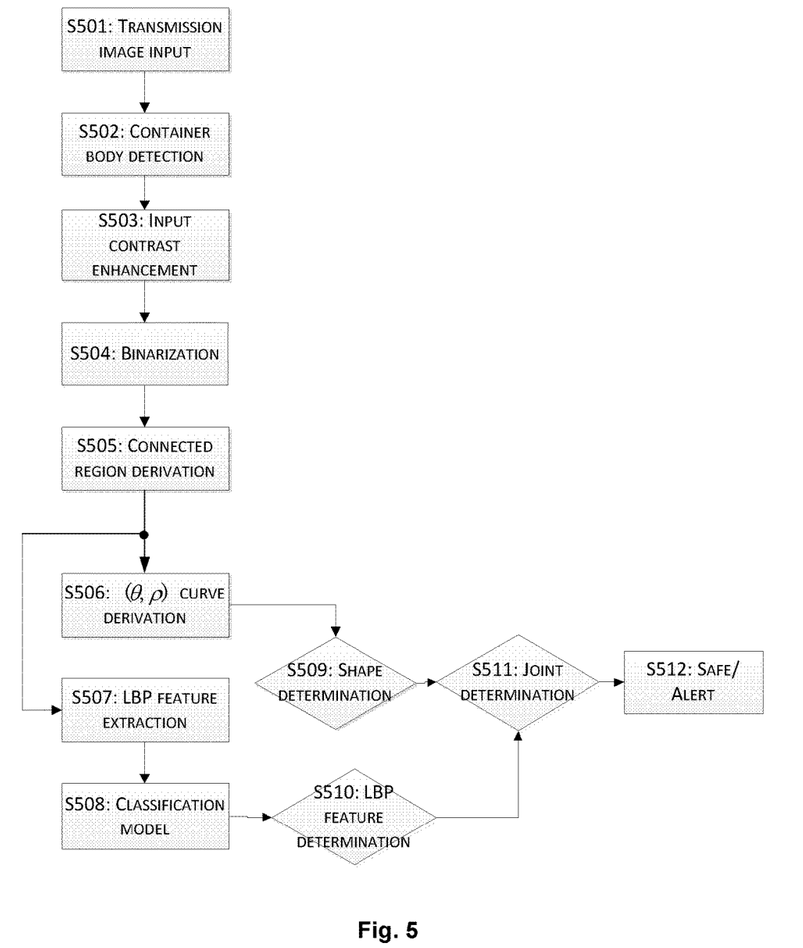
FIG. 5 is a flowchart illustrating a single energy mode according to an embodiment of the present disclosure.

FIG. 4 is a flowchart illustrating a method for inspection using a created model in a dual energy mode according to an embodiment of the present disclosure. FIG. 5 is a flowchart illustrating a single energy mode according to an embodiment of the present disclosure. An input to automatic detection of high atomic number matters can be a transmission image, or a transmission image and a material image (effective atomic number image). When a transmission image and a material image are inputted, the detection of high atomic number matters can be performed in accordance with the process shown in FIG. 4. When only a transmission image is inputted, the detection can be performed in accordance with the process shown in FIG. 5. Both FIG. 4 and FIG. 5 include steps of image inputting (S401, S411; S501); pre-processing (S402, S403; S502, S503), suspicious region generation (S404, S405; S504, S505), feature generation and determination (S407, S408, S409, S410; S507, S508, S509, S510), and outputting (S414; S512). Detailed description will be given with reference to FIG. 4 and FIG. 5.

In the dual energy mode, effective atomic number information of the inspected goods can be obtained from a high energy image and a low energy image. The information can be used, along with the shape information, to determine whether the image contains any high atomic number matter. At step S401, a transmission image is inputted.

Next, the inputted image is pre-processed. At step S402, a container region in the image is detected, such that the subsequent operations will be performed on the container image only, thereby reducing the amount of data to be processed. Then, at step S403, a contrast of the image is enhanced. For example, in order to improve the detection efficiency, a goods region can be obtained by applying a container body detection algorithm during the pre-processing phase, for subsequent detection of high atomic number matters. In order to increase the contrast, a logarithm conversion, or a logarithm conversion plus a square rooting operation, can be applied to the image and then the gray scale can be extended to 256 levels, so as to obtain the processed image. It can be appreciated by those skilled in the art that the above pre-processing operations can be omitted in some other embodiments.

At step S404, a series of binarization operations are performed on the initial image with the enhanced contrast. Assuming a step h of binarization, in the i-th binarization operation, pixel points each having a pixel value p satisfying 0≤p≤i*h(1≤i≤N) in the image are assigned with a value of 255 and the rest of pixels are assigned with 0. Then, at step S405, connected regions conforming to a specified size in these binarized images are derived and the upper, lower, left and right borders of these connected regions are recorded. In this way, a number of potential suspicious regions can be obtained.

The method then proceeds with the feature generation and determination process, in which feature information includes LBP features, shape features and/or material features. For example, at step S407, in the detection of the high atomic number matter, local texture features, such as LBP features, of the suspicious region are extracted. At step S408, the generated local texture features are inputted to the classification model to derive a class probability distribution. At step S408, it is determined based on the probability distribution whether the output resulting from the LBP features is suspicious or unsuspicious.

At step S406, all the suspicious regions are traversed and a contour line shape feature is extracted. For each suspicious region, a contour line of a suspicious object in the suspicious region can be obtained using an edge feature extraction algorithm such as Canny. Then, from the contour line, a centroid of the region enclosed by the contour line can be calculated. A $(\theta,\rho)$ curve of the contour line with respect to the centroid as a coordinate origin is derived. FIGS. 7A, 7B, 7C, 7D, 7E, 7F, 7G, 7H and 7I are schematic diagrams each showing a $(\theta,\rho)$ feature curve of a model of a high atomic number matter as used in the solution according to an embodiment of the present disclosure. In each of these figures, the horizontal axis represents an angle $\theta$ and the vertical axis represents an amplitude $\rho$.

Since the contour line is a set of discrete points, plus the diversity of the suspicious region, the derived $(\theta,\rho)$ curve is somewhat discontinuous. Hence, $\theta\_jump$ is used to record a maximum $\theta$ jump value of the $(\theta,\rho)$ curve. Let $S=\{x_1, x_2, \ldots, x_N\}$ denote the contour line and assuming that the points are arranged clockwise, the angle between two adjacent points with respect to the coordinate origin is $\Delta\theta=\{\theta_1, \theta_2, \ldots, \theta_N\}$. Here, $$\theta_{max} = \max_i\{\theta_i\}$$

is used for measuring the smoothness and discontinuity of the contour line and, when its value is larger than a given threshold $\theta_{thresh}$ (which is set to $\pi/6$ in this embodiment), there is a very low probability that a regular object is present in the suspicious region. Furthermore, there may be different numbers of points in different contour lines and thus the feature length of the derived $(\theta,\rho)$ may vary. It is required to adjust the feature lengths to 200 dimensions uniformly for similarity comparison between features. In addition, the contour line of the object may be simple or complex, and can be used as a dimensioning value of the border curve. Generally, a more complex curve has a larger number of dimensions. Hence, the number of dimensions can also be used as a feature index for determining the shape feature and complexity of the curve.

To simplify the calculation, in this embodiment, at step S409, the similarity between a shape of a hidden object in the suspicious region and a standard shape can be measured by Euclidian distance, amplitude consistency and $\theta$ jump value. For example, assuming that a contour line $S_0$ is characterized into a 200-dimension vector $V_0$ and a standard contour vector is $V_{st}$, the Euclidian distance between them is $L=|V_{st}-V_0|$ and the amplitude consistency is defined as a percentage P that the corresponding components are within the same value range. In this embodiment, when $L\leq4$, $P\geq0.9$ and $\theta_{max}\leq\pi/6$, the contour line $S_0$ is similar to the standard contour.

At step S411, a material image data is inputted. At step S412, a proportion of the pixel points of the high atomic number matter in the suspicious region is calculated. Based on a given threshold, it is possible to determine whether the current region contains a high atomic number matter in a more accurate manner. If only the transmission image data is received in the detection of the high atomic number matter, the determination can still be made. Based on the classification model that is trained in advance and the calculated shape feature of the suspicious region, it can be determined whether the transmission image contains a high atomic number matter.

At step S413, a joint determination is applied, which means two or more determination results will be considered jointly. Typically, the joint determination can be made by decision fusion. In the present disclosure, such determination is made by voting. That is, if two or more input determination results indicate "suspicious", an alert is given and the coordinates of the suspicious region is outputted; or otherwise a result of "unsuspicious" will be outputted. In some embodiments, the detection result of the high atomic number matter can be marked with a red rectangular frame, or otherwise highlighted.

FIG. 5 is a flowchart illustrating a single energy mode according to an embodiment of the present disclosure. Compared with the embodiment shown in FIG. 4, the embodiment shown in FIG. 5 does not have the input of the material image. That is, in the single energy mode, the determination as to whether the inspected goods contain any high atomic number matter is made based on the transmission image only. Hence, the steps S501-S510 in FIG. 5 are the same as the steps S401-S410, respectively. At step S511, the determination result based on the shape feature and the determination result based on the LBP feature are considered jointly. At step S512, the result is outputted, e.g., indicating that the goods are safe or providing an alert.

The above detailed description has already set forth numerous embodiments of the methods systems, and apparatuses for inspecting goods with reference to the diagrams, flow charts, and/or examples. In the case where the diagrams, flow charts, and/or examples comprise one or more functions and/or operations, one skilled in the art should appreciate that each function and/or operation in the diagrams, flow charts, or examples may be implemented by various structures, hardware, software, firmware or any combination thereof either alone and/or in any combination. In an embodiment, several parts of the subject matter described in the embodiments of the present disclosure may be implemented by Application Specific Integrated Circuit (ASIC), Field Programmable Gate Array (FPGA), Digital Signal Processor (DSP), or any other integrated form. However, one skilled in the art should appreciate that some aspects of the embodiment disclosed herein may be partially or wholly implemented in an integrated circuit effectively, implemented as one or more computer programs running on one or more computers (for example, one or more programs running on one or more computer systems), implemented as one or more programs running on one or more processors (for example, one or more programs running on one or more micro-processors), implemented as firmware, or substantially any combination thereof, and one skilled in the art is capable to design the circuit and/or write software and/or firmware code. Further, one skilled in the art would appreciate that the mechanism of the subject matter of the present disclosure may be distributed in various forms of program products, and the exemplary embodiments of the subject matter of the present disclosure may be applicable irrespective of the specific types of signal carrier media for distribution. Examples of the signal carrier media comprise but not limited to: a recordable medium such as floppy disk, hard drive, compact disk (CD), digital versatile disk (DVD), digital tape, computer memory, etc.; and a transmission medium, such as digital and/or analog communication medium (for example, optical fiber, waveguide, wired communication link, wireless communication link, etc.)

Although the present disclosure is already described with reference to several typical embodiments, it is to be appreciated that the terms used herein are illustrative and exemplary, rather than limiting. Since the present disclosure may be practice in multiple forms without departing from the spirit or essence, it is to be noted that the above embodiments are not limited to any previously described details and shall be interpreted broadly within the spirit and scope defined by the claims. Therefore, all changes and variations fall into the scope of the claims or their effectives shall be embraced by the claims.

The invention claimed is:

1. A method for inspecting goods comprising:
obtaining a transmission image of inspected goods;
processing the transmission image to obtain a suspicious region using a plurality of binarization operations;
extracting local texture features of the suspicious region and classifying the local texture features of the suspicious region based on a pre-created model to obtain a classification result;
extracting a contour line shape feature of the suspicious region and comparing the contour line shape feature with a pre-created standard template to obtain a comparison result; and
determining that the suspicious region contains a high atomic number matter if both the classification result and the comparison result indicate that the suspicious region contains the high atomic number matter;
wherein the extracting the contour line shape feature of the suspicious region comprises: deriving a contour line of the suspicious region using an edge extraction algorithm and deriving a ($\theta\rho$) feature curve of the contour line, where $\theta$ denotes an angle, and $\rho$ denotes an amplitude.

2. The method of claim 1, further comprising:
obtaining effective atomic number information of the suspicious region,
wherein the determining comprises determining that the suspicious region contains a high atomic number matter based on the classification result, the comparison result and the effective atomic number information.

3. The method of claim 1, wherein the processing the transmission image to obtain the suspicious region comprises:
enhancing a contrast of the transmission image;
performing the plurality of binarization operations on the contrast-enhanced transmission image; and
deriving a connected region of the binarized transmission image and determining a border of the connected region.

4. The method of claim 1, wherein the comparing the contour line shape feature with the pre-created standard template comprises:
calculating a distance and an amplitude consistency between the ($\theta,\rho$) feature curve of the contour line and the standard template and a $\theta$ jump value of the ($\theta,\rho$) feature curve of the contour line; and
comparing the distance, the amplitude consistency and the $\theta$ jump value with respective thresholds.

5. The method of claim 4, wherein a contour line of a suspicious object in the suspicious region is obtained using an edge feature extraction algorithm, a centroid of a region enclosed by the contour line is calculated, and then a ($\theta,\rho$) feature curve of the contour line with respect to the calculated centroid as a coordinate origin is derived.

6. The method of claim 1, further comprising:
highlighting a region considered to be the high atomic number matter in the transmission image.

7. A system for inspecting goods comprising:
an X-ray scanning device configured to obtain a transmission image of inspected goods; and
a data processing device configured to:
process the transmission image to obtain a suspicious region using a binarization operation;
extract local texture features of the suspicious region and classify the local texture features of the suspicious region based on a pre-created model to obtain a classification result;

extract a contour line shape feature of the suspicious region and compare the contour line shape feature with a pre-created standard template to obtain a comparison result; and determine that the suspicious region contains a high atomic number matter if both the classification result and the comparison result indicate that the suspicious region contains the high atomic number matter;

wherein the extracting the contour line shape feature of the suspicious region comprises: deriving a contour line of the suspicious region using an edge extraction algorithm and deriving a ($\theta\rho$) feature curve of the contour line, where $\theta$ denotes an angle, and $\rho$ denotes an amplitude.

\* \* \* \* \*